(12) United States Patent
Gasser

(10) Patent No.: US 7,578,726 B2
(45) Date of Patent: Aug. 25, 2009

(54) METHOD OF MANUFACTURING A CERAMIC SURGICAL INSTRUMENT

(75) Inventor: Matthias Gasser, Lage (DE)

(73) Assignee: Gebr. Brasseler GmbH & Co. KG, Lemgo (DE)

( * ) Notice: Subject to any disclaimer, the term of this patent is extended or adjusted under 35 U.S.C. 154(b) by 0 days.

(21) Appl. No.: 11/846,317

(22) Filed: Aug. 28, 2007

(65) Prior Publication Data

US 2008/0064303 A1    Mar. 13, 2008

(30) Foreign Application Priority Data

Sep. 12, 2006   (DE) .................. 10 2006 042 762

(51) Int. Cl.
*B24B 7/19* (2006.01)
(52) U.S. Cl. .......................................... 451/48; 451/57
(58) Field of Classification Search .................. 451/28, 451/47, 48, 57, 58, 44, 45, 56, 59

See application file for complete search history.

(56) References Cited

U.S. PATENT DOCUMENTS

| 5,564,966 A * | 10/1996 | Nishioka et al. ............... 451/41 |
| 6,220,933 B1 * | 4/2001 | Shih et al. ..................... 451/28 |
| 2006/0127847 A1 | 6/2006 | Danger et al. |

FOREIGN PATENT DOCUMENTS

| DE | 2738 | 1/1953 |
| DE | 203 14 717 U1 | 2/2004 |
| DE | 102 02 954 B4 | 7/2006 |
| JP | 05220669 A * | 8/1993 |
| WO | WO 03/061898 A1 | 7/2003 |

* cited by examiner

*Primary Examiner*—Dung Van Nguyen
(74) *Attorney, Agent, or Firm*—Pearne & Gordon LLP

(57) ABSTRACT

The invention relates to a method of manufacturing a surgical instrument having a rotatable shaft 2 and a working part 1 disposed thereon, the working part having at least one cutting edge, wherein the shaft 2 and the working part 1 are made of oxide ceramics, characterized in that for the manufacturing of the contour of the instrument, a rough grinding using a grinding tool having a grain size between 40 µm and 110 µm is performed, and subsequently, a fine grinding of the cutting edges using a grinding tool having a grain size between 20 µm and 50 µm performed.

14 Claims, 1 Drawing Sheet

METHOD OF MANUFACTURING A CERAMIC SURGICAL INSTRUMENT

The invention relates to a method of manufacturing a surgical instrument according to the preamble portion of claim 1.

In detail, the invention relates to a method of manufacturing a surgical instrument, in which at least the working part (head) is made of a ceramic material, in particular oxide ceramics.

From the state of the art, different methods of manufacturing ceramic tools are pre-known. In many cases, a mold was produced from a pre-sintered ceramic material (green compact), wherein the relatively soft ceramic material may be machined in a simple manner. Subsequently, the green compact is readily sintered while having a correspondingly decreased dimension. In this context, it has proven to be disadvantageous that the dimensional stability is not guaranteed sufficiently to produce dental instruments or surgical instruments which rotate at high speeds.

DE 203 14 717 U1 describes a ceramic instrument in the form of a drill, in which the working part is made of a ceramic material and which features a surface roughness of 0.5 to 6 µm.

DE 102 02 954 B4 describes a manufacturing method for a rod-shaped drill, in which pre-shaped body having a straight inner recess is twisted and subsequently finished.

DD 2738 describes a method for countersinking threads in cylindrical ceramic bodies by means of a profiled grinding wheel.

It is an object of the invention to provide a method of the aforementioned kind, which is suited for the manufacturing of surgical instruments and dental instruments having a high quality, while having a simple structure and a simple and cost-effective feasibility.

According to the invention, the object is solved by the combination of features of claim 1, the sub-claims show further advantageous embodiments of the invention.

According to the invention, it is thus provided that, in a first production step for manufacturing the contour of the surgical instrument or dental instrument, a rough grinding using a grinding tool having a rain size between 40 µm and 110 µm, and in particular a grain size of between 44 µm and 105 µm, is performed, and that subsequently a fine grinding of the cutting edges of the surgical instrument or dental instrument using a grinding tool having a grain size between 20 µm and 50 µm, and in particular a grain size of between 20 µm and 44 µm, is performed.

Due to the inventive selection of the grain sizes of the grinding tools, which may be formed preferably cylindrical and may be contoured at their peripheries, a processing with high quality and high efficiency is secured, without a danger of damaging the ceramic material. This is particularly important for surgical instruments or dental instruments having very small dimensions, in particular very small diameters.

The inventive surgical instruments may be formed as drills or milling cutters, wherein the working parts may be formed cylindrically, spherically, conically or in any other way.

In a preferred further development of the invention, it is provided that the cutting speed is between 30 m/sec and 70 m/sec. In this context, it is particularly advantageous if the feed rate is between 1 mm/min and 10 mm/min. Therewith, there results the possibility of a high quality and economic manufacturing of the ceramic surgical instrument or dental instrument.

For finishing the cutting edges in a further step, it may be particularly advantageous to select a cutting speed of 25 m/sec, while the feed rate is between 20 mm/min and 40 mm/min.

For finishing the cutting edges of the working part, it may also be preferable to provide a grain size of 20 to 50 µm.

The selection of the cutting conditions is also dependent on the respective dimensions, in particular the diameter and the cutting edge geometry of the surgical instrument or dental instrument.

In a particularly advantageous embodiment of the invention, it is provided that the grinding tool comprises a grinding body having abrasive grains which comprise or consist of diamond grains.

The bonding of the grinding grains of the grinding wheels may be performed in the form of a sintered metal bond, a ceramic bond or a resin bond.

Concerning the manufacturing of the surgical instruments or dental instruments, there result different variations according to the invention. It is possible to produce at first a shaft from a preferably cylindrical basic material. Subsequently, the contour of the working part or head is ground and the working part or head is provided with cutting edges in one production step. After completing the working part or head, a finishing of the clamping portion of the shaft may be performed. It is, however, also possible to change the sequence of processing, e.g. to grind the contour of the working part/head as well as of the shaft in one production step.

The cylindrical semi-finished part to be used may be manufactured by a sinter process and a subsequent HIP treatment (HIP—hot isostatic pressing). However, it is also possible to manufacture the basic semi-finished part by means of an extrusion or injection molding process.

In a similar manner, it is also possible according to the invention, to produce the working part from a ceramic material and to produce the shaft from a metallic material, wherein the working part and the shaft may e.g. be connected by soldering.

Furthermore, according to the invention, it may be preferable to perform the grinding process supported by ultrasound in order to support the abrasive effect of the grinding tool.

According to the invention, it is possible to use different grinding methods, e.g. grinding processes with non-fixed working part, peel grinding or round grinding.

In the following, the invention is described on the basis of an embodiment in combination with the drawing, in which:

FIG. 1 shows a cylindrical basic material which was rough-ground with respect to its outer diameter and its end dimensions. In the state shown in FIG. 2, the working part 1, which was already processed in FIG. 1 with respect to its outer diameter, is clamped to finish or fine-ground the shaft 2.

Figure 1:
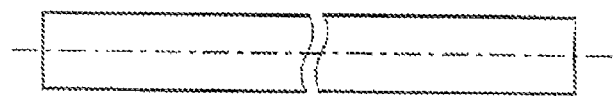
FIG. 1 shows a schematic view of a semi-finished part or basic material.
Figure 2:
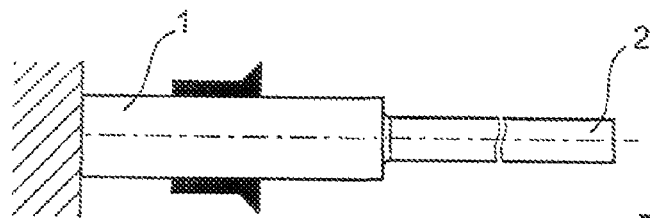
FIG. 2 shows a state in which a shaft is rough-ground.
Figure 3:
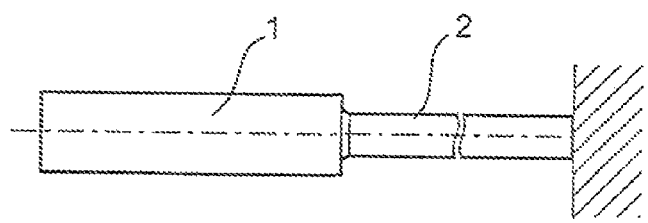
FIG. 3 shows a state in which a working part/head is rough-ground.
Figure 4:
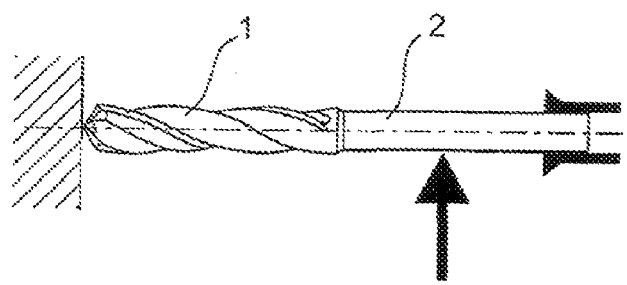
FIG. 4 shows a state in which the head/working part is finished.
Figure 5:
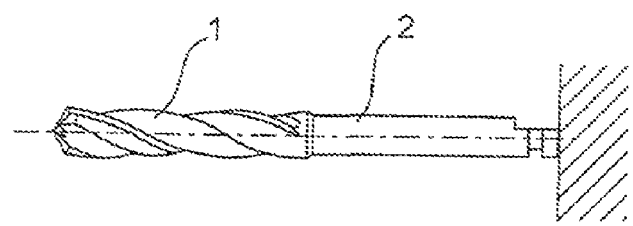
FIG. 5 shows a state in which the shaft end is finished.

In the state shown in FIG. 3, a calibration or pre-processing of the head/working part 1 is performed. In the subsequent production step, the shaft 2 is clamped, while the cutting edges at the working part/head 1 are finished. According to FIG. 5, the end of the shaft 2 is subsequently processed in order to produce the corresponding clamping portion.

The invention claimed is:

1. A method of manufacturing a surgical instrument having a rotatable shaft (2) and a working part (1) disposed thereon, the working part having at least one cutting edge, wherein at least the working part (1) is made of oxide ceramics, the method comprising:
   manufacturing a contour of the instrument, including the working part (1), by a rough grinding of the instrument, including the working part (1), using a grinding tool having a grain size between 40 µm and 110 µm; and
   subsequent to the manufacturing of the contour of the working part (1), fine grinding the at least one cutting edge in the working part (1) using a grinding tool having a grain size between 20 µm and 50 µm.

2. The method of claim 1, wherein a cutting speed between 30 m/sec and 70 m/sec is selected.

3. The method of claim 2, wherein a feed rate of the grinding tool between 1 mm/min and 10 mm/min is selected.

4. The method of claim 1, wherein a feed rate of the grinding tool between 1 mm/min and 10 mm/min is selected.

5. The method of claim 1, wherein a grinding tool having diamond grains as abrasive particles is used.

6. The method of claim 5, wherein a grinding tool is used, in which the grinding grains are bound by a sintered metal bond.

7. The method of claim 5, wherein a grinding tool is used, in which the grinding grains are bound by a ceramic bond.

8. The method of claim 5, wherein a grinding tool is used, in which the grinding grains are bound by a resin bond.

9. The method of claim 1, wherein at first the shaft (2) and subsequently the working part (1) with the at least one cutting edge are formed from a blank.

10. The method of claim 1, wherein at first the working part (1) with the at least one cutting edge and subsequently the shaft (2) are formed from a blank.

11. The method of claim 1, wherein at first the contour of the working part (1) and subsequently the at least one cutting edge are formed.

12. The method of claim 1, wherein the at least one cutting edge is completely ground in one production step.

13. The method of claim 1, wherein the at least one cutting edge is at first rough-ground and then finished.

14. The method of claim 1 wherein both the rotatable shaft (2) and the working part (1) are made of oxide ceramics.

* * * * *